(12) United States Patent
Nakagoshi et al.

(10) Patent No.: US 7,691,597 B2
(45) Date of Patent: Apr. 6, 2010

(54) METHOD FOR MEASURING PROTEASE ACTIVITY OF TRANSGLUTAMINASE AND TRANSGLUTAMINASE COMPOSITION

(75) Inventors: Hiroyuki Nakagoshi, Kawasaki (JP); Rikiya Ishida, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 554 days.

(21) Appl. No.: 11/512,109

(22) Filed: Aug. 30, 2006

(65) Prior Publication Data

US 2007/0054346 A1 Mar. 8, 2007

Related U.S. Application Data

(60) Provisional application No. 60/712,087, filed on Aug. 30, 2005.

(30) Foreign Application Priority Data

Aug. 30, 2005 (JP) .............................. 2005-248767

(51) Int. Cl.
C12Q 1/37 (2006.01)

(52) U.S. Cl. ...................................................... 435/23

(58) Field of Classification Search ........................ None
See application file for complete search history.

(56) References Cited

U.S. PATENT DOCUMENTS

| 5,518,742 | A | 5/1996 | Soeda et al. |
| 5,658,605 | A | 8/1997 | Soeda et al. |
| 5,968,568 | A | 10/1999 | Kuraishi et al. |
| 2004/0131728 | A1 | 7/2004 | Ootsuka et al. |
| 2005/0037128 | A1* | 2/2005 | Kimura et al. .............. 426/643 |
| 2005/0249839 | A1 | 11/2005 | Ishida et al. |
| 2007/0202213 | A1 | 8/2007 | Ishida et al. |

OTHER PUBLICATIONS

Kobayashi et al. "Transglutaminase in sporulating cells of *Bacillus subtilis*", J. Gen, Appl, Microbiol. 1998, 44:85-91.*
U.S. Appl. No. 12/566,901, filed Sep. 25, 2009, Ishida, et al.
U.S. Appl. No. 08/563,587, filed Nov. 28, 1995, Sakai, et al.

* cited by examiner

*Primary Examiner*—Karen Cochrane Carlson
*Assistant Examiner*—Bin Shen
(74) *Attorney, Agent, or Firm*—Oblon, Spivak, McClelland, Maier & Neustadt, L.L.P.

(57) ABSTRACT

The invention provides a method for measuring the protease activity of a transglutaminase-containing product comprising: mixing an aqueous solution (sample solution) of a transglutaminase-containing product and an aqueous solution of dimethylcasein in a prescribed ratio of transglutaminase activity to quantity of dimethylcasein, allowing the mixture to stand under prescribed conditions to cause a degradation reaction by protease to progress, adding an acid, filtering, and measuring the concentration of the protein in the filtrate. The invention is particularly useful for transglutaminase formulation for binding application and transglutaminase formulation for Surimi product.

19 Claims, 1 Drawing Sheet

METHOD FOR MEASURING PROTEASE ACTIVITY OF TRANSGLUTAMINASE AND TRANSGLUTAMINASE COMPOSITION

CROSS-REFERENCES TO RELATED APPLICATIONS

The present application claims the benefit of U.S. Provisional Application No. 60/712,087 filed on Aug. 30, 2005, and Japanese Patent Application No. 2005-248767 filed on Aug. 30, 2005, the entire contents of which are hereby incorporated by reference.

BACKGROUND OF THE INVENTION

1. Technical Field of the Invention

The present invention relates to a method for measuring the protease activity of transglutaminase-containing products that are useful as enzyme additives in protein-containing materials, and to methods for preparing transglutaminase formulation for binding application. In particular, the present invention relates to a method for measuring the protease activity in transglutaminase-containing products, this protease activity being closely related to the functioning of transglutaminase in binding application and Surimi products; methods of preparing transglutaminase-containing products in which the protease activity is regulated based on the value of the protease activity measured by this measurement method; and transglutaminase formulations, manufactured according to these preparation methods for binding application and Surimi products, in which protease activity is regulated.

2. Background Description

Transglutaminase is an enzymatic substance known to modify the physical properties of protein-containing materials. It is added directly to protein-containing materials to modify their physical properties, or is mixed with protein-containing materials, particularly gelatins and milk protein solutions, and employed in various substances as binding composition. However, transglutaminase formulations manufactured using available transglutaminase-containing products, particularly transglutaminase-containing products derived from microbes, vary greatly in quality from lot to lot in the same manner as other enzymatic formulations.

The principal reason for the variation between lots in the effectiveness of transglutaminase formulations in protein-containing materials is thought to be variation in the transglutaminase activity of the transglutaminase-containing product. However, variation in quality remains even when transglutaminase activity is controlled, constituting a major operational problem.

There have also been cases in which the presence of protease has been suspected of causing change in protein-containing materials to which transglutaminase-containing products have been added. However, the correlation between change and protease activity in transglutaminase-containing products measured by conventional methods of measuring protease activity has been extremely low, and there have not been any cases in which protease has been determined to be the cause. Since the cause of the variation in quality has been, unclear in this manner, ensuring the quality of a formulation has required countermeasures such as sorting by testing and increasing the blending ratio of transglutaminase-containing product to achieve a surplus. However, both of these methods entail increased labor and starting material costs, driving up the cost of manufacturing a formulation. Thus, once the reason is discovered, there is great need for a quality control technique based on an index with a high correlation with quality for both transglutaminase-containing products and transglutaminase formulations manufactured using such products.

Examples of undesired protease being present in or contaminating a protein-containing material, thereby negatively affecting the material, have been known for some time. However, the quantity producing an effect varies with the type and use of protein-containing materials in which this occurs, as well as with the type and origin of the protease. Further, a number of methods of measuring protease activity have been proposed. However, the correlation between the protease activity value that is measured and the magnitude of the effect on the protein-containing material is not necessarily high. Thus, these methods have afforded low reliability as quality control methods for protease activity.

In transglutaminase derived from microbes, there is a known example of the intentional formulation of protease in prescribed applications (Japanese Patent Application Publication No. H07-023740). An example of an attempt to control the effect of residual protease in a protein-containing material enhanced with transglutaminase is also known (Japanese Patent Application Publication No. H9-299065). However, there is no known case of measuring the effect on food of protease present as an impurity in a transglutaminase-containing product and attempting to regulate it.

Known methods of selectively deactivating protease in enzyme-containing products include a method of eliminating the activity of enzymes present as impurities, such as protease and α-amylase, by a 16 hour treatment at 37° C. and pH 9.8 (Japanese Patent Application Publication No. H11-42086) and a method of deactivating the protease present in lactase by irradiation with γ-rays (Japanese Patent Application Publication No. S54-18349).

However, there is no description suggesting any relation with effects such as the binding strength of transglutaminase-containing products in which protease activity has been decreased by these methods or improved physical properties in Surimi products.

There is literature (2$^{nd}$ Ed., *Self-Imposed Standards for Food Additives Other than Chemically Synthesized Products*, published by the Japan Food Additive Association, pp. 215-223 (1993)) relating to methods of measuring the activity of common proteases (papain, pancreatin, bromelain, and pepsin). However, there is no description suggesting any correlation between the value of the protease activity in a transglutaminase-containing product measured by this method and binding strength when this transglutaminase-containing product is employed as a binding component, in a formulation for Surimi products, or to produce a physical property-enhancing effect in Surimi products.

SUMMARY OF THE INVENTION

The present inventors conducted extensive research, resulting in the discovery that the correlation between protease activity and the quality of a transglutaminase formulation increased when the conditions of the enzymatic reaction in a protease activity measurement method, specifically, the reaction temperature and the transglutaminase activity/substrate ratio, approached the conditions of the protein-containing material following addition of the transglutaminase formulation. Thus, the cause behind the variation in quality of transglutaminase formulations was presumed to be the protease contained in the transglutaminase-containing material. Further, protease can be regulated with extremely high precision by the method of the present invention, permitting stabilization of the quality of transglutaminase formulations.

One object of the present invention is to provide a method of measuring protease activity in transglutaminase-containing products and formulations. In protein-containing materials, particularly transglutaminase-containing products employed as main ingredients in restructured food products and Surimi products, this protease activity correlates closely with the quality of a formulation, particularly the binding strength of an formulation for binding application, as well as the enhancement effect on the physical properties of Surimi in Surimi formulations.

Further objects of the present invention are to provide methods of preparing transglutaminase formulations for use in various materials, particularly transglutaminase formulations for binding application and Surimi products, by employing a protease activity value as index, selecting transglutaminase-containing materials having a prescribed protease activity that have been obtained according to the above-described measurement method, and employing the selected transglutaminase-containing products, either singly or in combination with other materials; and to provide formulations prepared by this method.

To solve the above-stated problem, the present invention essentially relates to a method of measuring protease activity in a transglutaminase-containing product. This method comprises: mixing an aqueous solution of transglutaminase-containing product (sample solution) with an aqueous solution of protease substrate in the form of dimethylcasein in a prescribed ratio of transglutaminase activity to the quantity of dimethylcasein; conducting a protease degradation reaction to progress under prescribed conditions; adding an acid; and measuring the quantity of protein in the solution.

Based on the method of the present invention, the prescribed ratio of enzyme to substrate and suitable reaction temperature vary with the application. For transglutaminase formulation for binding application, the ratio of transglutaminase activity to substrate weight is desirably 200 or less, with a reaction temperature of 0° C. or more and 10° C. or less being desirable. In transglutaminase formulations for Surimi products, the ratio of transglutaminase activity to substrate weight is desirably 200 or less, with a reaction temperature of 30° C. or more and 50° C. or less being desirable.

The present invention covers the following specific inventions.

(1) A method for measuring the protease activity of a transglutaminase-containing product comprising:
(a) preparing an aqueous solution of a transglutaminase-containing product and an aqueous solution of a protease substrate in the form of dimethylcasein so that the ratio of transglutaminase activity to the quantity of dimethylcasein is 200 units/g or less;
(b) conducting an enzymatic reaction based on protease;
(c) adding an acid and filtering; and
(d) measuring the concentration of the protein in the filtrate.
(2) The method for measuring the protease activity of a transglutaminase-containing product according to (1), wherein said enzymatic reaction based on protease is conducted at a temperature of not less than 0° C. and not greater than 10° C.
(3) The method for measuring the protease activity of a transglutaminase-containing product according to (1), wherein measurement of the protease activity in the transglutaminase-containing product is conducted under the following conditions:
(I-a) preparing a solution of sample transglutaminase-containing product and a solution of protease substrate in the form of dimethylcasein in a such a manner as to yield 2.4 parts of a pH 6 aqueous solution with a transglutaminase activity of 83.3 units/100 mL and a dimethylcasein content of 2.083 g/100 mL;
(I-b) conducting an enzymatic reaction based on the protease by mixing the solution of transglutaminase-containing product and aqueous solution of dimethylcasein and allowing the mixture to stand for 24 hours at 5° C.;
(I-c) obtaining a sample filtrate by adding two parts of 12 percent trichloroacetic acid, centrifuging the mixture, and filtering the supernatant;
(II-a) preparing two parts of a pH 6 aqueous solution comprising 2.5 g/100 mL of dimethylcasein solution;
(II-b) allowing the dimethylcasein aqueous solution to stand for 24 hours at 5° C.;
(II-c) adding two parts of 12 percent trichloroacetic acid, adding 0.4 part of a solution of 500 units/100 mL of sample transglutaminase-containing product, mixing, centrifuging the mixture, and filtering the supernatant to obtain a blank filtrate;
(d) causing a coloration reaction by the Lowry method in the sample solution and blank filtrate, measuring the absorbance of each solution at a wavelength of from 500 to 700 nm employing distilled water as control, denoting the absorbance of the sample filtrate as A1 and the absorbance of the blank filtrate as A2, separately causing a coloration reaction by the Lowry method in standard purified bovine serum albumin solution of known concentration, measuring the absorbance at a wavelength of from 500 to 700 nm employing distilled water as control, creating a calibration curve from the absorbance of the standard purified bovine serum albumin solution and the absorbance of the distilled water, calculating the protein concentration of the sample filtrate and blank (PA1, PA2) from absorbance values A1 and A2, and obtaining the protease activity from the following equation:

$$\text{protease activity (units/g)} = (PA1 - PA2) \times 4.4 \div 0.4 \div 1440 \times V \div W$$

wherein:
PA1 denotes the protein concentration of the sample filtrate (mg BSA/mL);
PA2 denotes the protein concentration of the blank (mg BSA/mL);
4.4÷0.4 denotes the coefficient of conversion to the total quantity of the solution at the end of the reaction;
1440 denotes the number of minutes in a reaction time of 24 hours;
V denotes the dissolved volume of sample transglutaminase-containing product (mL); and
W denotes the quantity of sample transglutaminase-containing product employed (g).
(4) A method for preparing a transglutaminase formulation for binding application comprising:
(a) measuring the protease activity of multiple types of transglutaminase-containing products by the measurement method of any one of (1) to (3); and
(b) selecting and employing a transglutaminase-containing product with a ratio of protease activity to transglutaminase activity (units of protease activity/units of transglutaminase activity) of 0.00024 or less.
(5) A method for preparing a transglutaminase formulation for binding application comprising:
(a) conducting measurement according to the method for measuring the protease activity of a transglutaminase-containing product described in any one of (1) to (3); and (b) employing a protein-containing material and a transglutaminase-containing product with a ratio of protease activity to transglutaminase activity (units of protease activity/units of transglutaminase activity) of 0.00024 or less for use.

(6) The method for preparing a transglutaminase formulation for binding application according to (5) wherein said protein-containing material is gelatin.

(7) A transglutaminase formulation for binding application of food prepared according to the preparation method described in (4).

(8) A transglutaminase formulation for binding application of food prepared according to the preparation method described in (5).

(9) A transglutaminase formulation for binding application of food prepared according to the preparation method described in (6).

(10) The method for measuring the protease activity of a transglutaminase-containing product according to (1) comprising conducting an enzymatic reaction based on said protease at a temperature of not less than 30° C. but not greater than 50° C.

(11) The method for measuring the protease activity of a transglutaminase-containing product according to (1), wherein measurement of the protease activity in the transglutaminase-containing product is conducted under the following conditions:

(I-a) preparing a solution of sample transglutaminase-containing product and a solution of protease substrate in the form of dimethylcasein in a such a manner as to yield 2.4 parts of a pH 6 aqueous solution with a transglutaminase activity of 83.3 units/100 mL and a dimethylcasein content of 2.083 g/100 mL;

(I-b) conducting an enzymatic reaction based on the protease by mixing the solution of transglutaminase-containing product and aqueous solution of dimethylcasein and allowing the mixture to stand for 1 hour at 40° C.;

(I-c) obtaining a sample filtrate by adding two parts of 12 percent trichloroacetic acid, centrifuging the mixture, and filtering the supernatant;

(II-a) preparing two parts of a pH 6 aqueous solution comprising 2.5 g/100 mL of dimethylcasein solution;

(I-b) allowing the dimethylcasein aqueous solution to stand for 1 hour at 40° C.;

(II-c) adding two parts of 12 percent trichloroacetic acid, adding 0.4 part of a solution of 500 units/100 mL of sample transglutaminase-containing product, mixing, centrifuging the mixture, and filtering the supernatant to obtain a blank filtrate;

(d) causing a coloration reaction by the Lowry method in the sample solution and blank filtrate, measuring the absorbance of each solution at a wavelength of from 500 to 700 nm employing distilled water as control, denoting the absorbance of the sample filtrate as A1 and the absorbance of the blank filtrate as A2, separately causing a coloration reaction by the Lowry method in standard purified bovine serum albumin solution of known concentration, measuring the absorbance at a wavelength of from 500 to 700 nm employing distilled water as control, creating a calibration curve from the absorbance of the standard purified bovine serum albumin solution and the absorbance of the distilled water, calculating the protein concentration of the sample filtrate and blank (PA1, PA2) from absorbance values A1 and A2, and obtaining the protease activity from the following equation:

$$\text{protease activity (units/g)} = (PA1 - PA2) \times 4.4 \div 0.4 \div 60 \times V \div W$$

wherein:
PA1 denotes the protein concentration of the sample filtrate (mg BSA/mL);
PA2 denotes the protein concentration of the blank (mg BSA/mL);
4.4÷0.4 denotes the coefficient of conversion to the total quantity of the solution at the end of the reaction;
60 denotes the number of minutes in a reaction time of 1 hour;
V denotes the dissolved volume of sample transglutaminase-containing product (mL); and
W denotes the quantity of sample transglutaminase-containing product employed (g).

(12) A method for preparing a transglutaminase formulation for Surimi products, comprising:

(a) measuring the protease activity of multiple types of transglutaminase-containing products by the measurement method of claim (1), (10), or (11); and (b) selecting and employing a transglutaminase-containing product with a ratio of protease activity to transglutaminase activity (units of protease activity/units of transglutaminase activity) of 0.002 or less.

(13) A method for preparing a transglutaminase formulation for Surimi products, comprising:

(a) conducting measurement according to the method for measuring the protease activity of a transglutaminase-containing product described of (1), (10), or (11); and (b) employing a transglutaminase-containing product with a ratio of protease activity to transglutaminase activity (units of protease activity/units of transglutaminase activity) of 0.002 or less, and at least one additional component selected from the group consisting of calcium salts, alkali salts, and protein-containing materials.

(14) A transglutaminase formulation for Surimi products prepared according to the preparation method described in claim (12).

(15) A transglutaminase formulation for Surimi products prepared according to the preparation method described in (13).

Based on the method for measuring protease activity of the present invention, the effect of the transglutaminase formulation when employed in a protein-containing material can be readily determined from the protease activity of the transglutaminase-containing product.

Further, application of the above-described measurement method permits the ready selection of a transglutaminase-containing product that can be used to constitute a transglutaminase formulation exhibiting desired effects from various available transglutaminase-containing products.

Further, application of the above-described measurement method permits the ready selection of a transglutaminase-containing product that can be used to constitute a transglutaminase formulation exhibiting desired binding effects from various available transglutaminase-containing products.

Further, application of the above-described measurement method permits the ready selection of a transglutaminase-containing product that can be used to constitute a transglutaminase formulation exhibiting desired effects on Surimi products from various available transglutaminase-containing products.

DETAILED DESCRIPTION OF THE PREFERRED EMBODIMENTS

Figure 1:
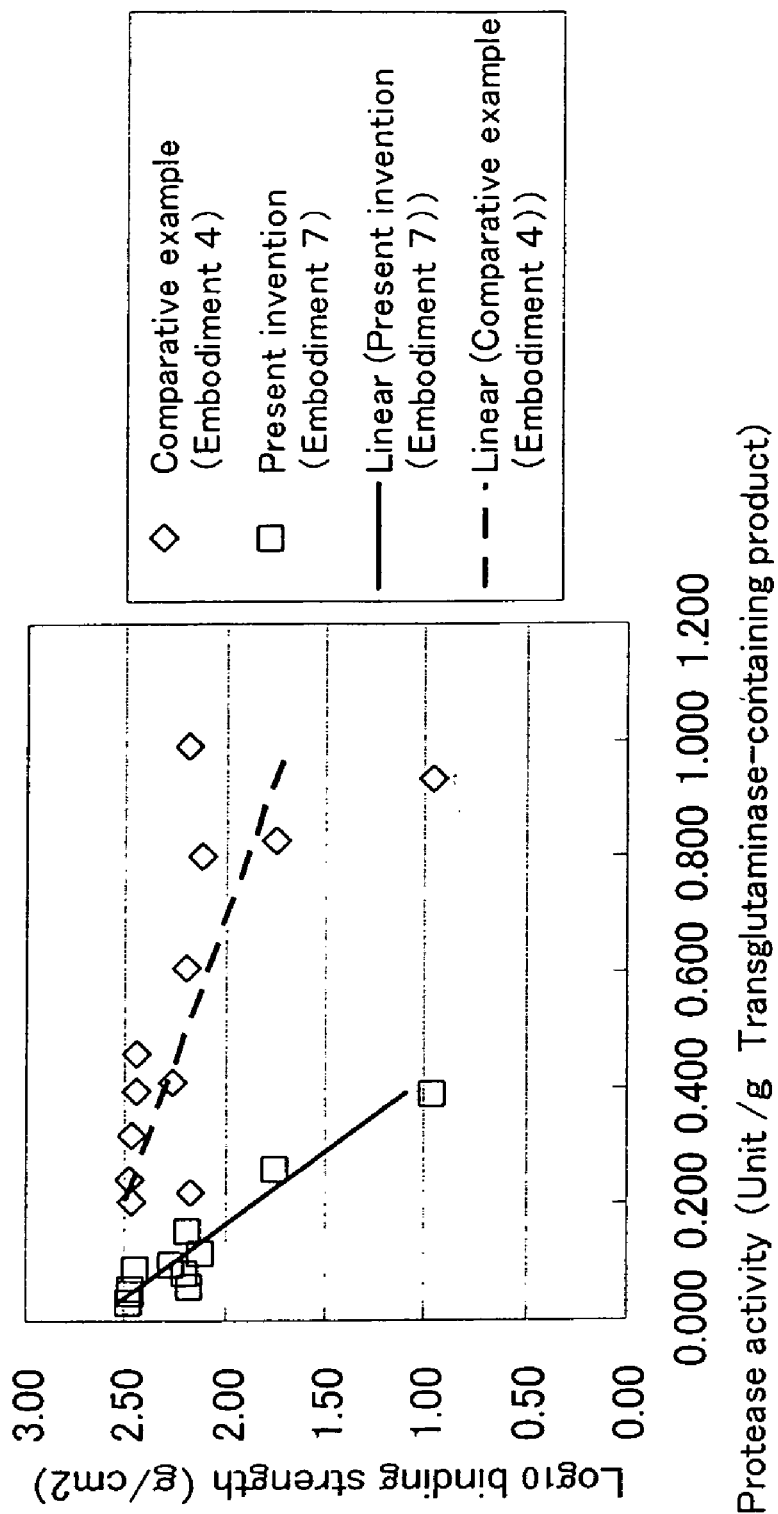
FIG. 1 is a graph showing the correlation between the protease activity in glutaminase by the measurement method of the present invention and binding strength.

Implementation modes of the present invention are described below.

The present inventors discovered that the effectiveness of a transglutaminase formulation containing a transglutaminase-containing product varied between the lots of transglutaminase-containing product that were employed, and that there was considerable variation that did not depend on transglutaminase activity. They also discovered that when a transglutaminase-containing product of low effectiveness was mixed with a protein-containing material and left standing, there was considerable decrease over time in the molecular weight of the protein. Based on these phenomena, the protease contained in the transglutaminase-containing product was investigated.

In addition to transglutaminase activity, a trial production test in which the final product for a given application is actually prepared can be cited as an example of an index of quality control for transglutaminase formulations. In such a trial production test, secondary factors such as fluctuation in the level of effectiveness of the transglutaminase and in the quality of the trial product itself due to the type and quality of starting materials, the superiority of the trial production technique, and the like have substantial effects. Thus, reproducibility is inadequate and a trial production test cannot be considered a desirable index of quality control for transglutaminase formulations.

One example of a method of controlling the quality of transglutaminase-containing products for formulations for binding application is measurement of the binding strength by a binding test. However, even when transglutaminase-containing products from the same lot are employed, the binding strength varies each day the test is conducted due to the type and quality of meat. Adequate reproducibility is thus difficult to achieve. Thus, such measurement is not necessarily desirable as an index of quality control for formulations for binding application. The trail production of boiled fish paste and the measurement of the physical properties of such paste are similarly undesirable as methods of quality control for transglutaminase-containing products employed in formulations for use in Surimi products.

Generally, enzymatic activity, including protease activity, can usually be measured at the maximum temperature at which the enzyme is stable. When enzymatic properties are not known, a reaction temperature near the 37° C. body temperature of mammals can often be employed. Further, it is necessary to achieve adequate detection sensitivity for an adequate number of protein degradation products by the method of detecting protein degradation products employed. Generally, the reaction time is determined ahead of time to shorten the time required for measurement, and the quantity of enzyme added is set large enough to achieve the required detection sensitivity.

Based on investigation by the present inventors, there was low correlation between the activity of protease contained in transglutaminase-containing products when measured under normal conditions and the quality of formulations for binding application and formulations for Surimi products. For example, with the ratio of transglutaminase activity to substrate weight set to 2,000 units/g, the reaction temperature set to 37° C., the reaction time set to one hour, and other conditions set based on these preconditions, only low correlations were achieved between the values of the protease activity of transglutaminase-containing products from multiple lots that were measured on the one hand, and the binding strength of formulations for binding application prepared using these transglutaminase-containing products and the effects produced in Surimi product formulations and Surimi products on the other.

Thus, it is difficult to control the quality of transglutaminase formulations based on the results of the measurement of protease activity under such general conditions.

The present inventors conducted extensive research into conditions used to measure protease activity that correlated well with the quality of transglutaminase formulations. As a result, they developed the above-described measurement method. The protease activity measured by this method can be employed as an index, transglutaminase-containing product having protease activity within a prescribed range can be selected, and transglutaminase formulations can be manufactured, making it possible to provide stable, quality formulations.

When devising the present invention, a characteristic running counter to commonly held notions was discovered whereby the enzyme concentration dependency and temperature dependency of the activity of protease present as an impurity in transglutaminase-containing products varied greatly by lot. The discovery of this characteristic was important. The facts that two or more proteases were present in transglutaminase-containing products, that the content ratios of these proteases varied by lot, that an inhibiting factor for one of these proteases was contained in transglutaminase-containing products, that the content of this inhibiting factor varied by lot, and that, contrary to the commonly held notion, this inhibiting factor was the cause of these differing enzyme characteristics were discovered by the present inventors.

In the present invention, the term "protease" refers to enzyme-degrading proteins that are present either due to migration from starting materials in the course of manufacturing a transglutaminase-containing product or through secretion by microbes.

In the present invention, the term "transglutaminase" refers to a type of transferase that catalyzes an acyl transfer reaction.

The transglutaminase employed in the present invention may be derived from tissue or from microbes. However, microbial transglutaminase is desirable because of its low cost. The transglutaminase employed in the present invention may be calcium-dependent or calcium-independent. Calcium-independent transglutaminase is desirable from the perspective of having an effect that is independent of the calcium concentration of the material to which it is added.

In the present invention, the term "transglutaminase-containing product" means a liquid, or powder obtained by drying such a liquid, that is obtained from organic tissue or a microbial culture solution containing transglutaminase and then subjected to filtration and purification steps as needed. Excipients and stabilizing agents may be admixed to render the transglutaminase activity uniform or stabilize enzymatic activity.

In the present invention, the term "transglutaminase formulation" refers to a mixture of a transglutaminase-containing product and one or more additional components selected based on the objective. Here, the term "additional component" means a protein-containing-material, salt, sugar, excipient, or the like.

In the present invention, the "protein-containing material" to which the transglutaminase-containing product or transglutaminase formulation is added is a material containing a protein comprising glutamine residues serving as substrate for transglutaminase, and may be edible or inedible. Examples of edible protein-containing materials are materials derived from vegetable proteins, animal proteins, microbial proteins, and algal proteins. Examples of vegetable proteins are soy protein, wheat protein, and pea protein. Examples of animal proteins are livestock meat, poultry, fish, chicken eggs, milk, isolated purified products thereof, fish roe, blood plasma protein, gelatin, and collagen.

Calcium lactate, calcium carbonate, calcinated calcium, trisodium phosphate, sodium carbonate, and the like are readily employed salts. Examples of sugars suitable for use include sugars, starches, dextrin, and sugar alcohols. The above sugars can be employed as excipients. Dextrin, starches, lactose, and the like, which have little effect on flavor, are particularly desirable.

The acid in the present invention is added to cause any dimethylcasein that has not been degraded by protease to aggregate so that it can be separated and eliminated by subsequent centrifugation. Any acid that causes aggregation of dimethylcasein may be employed. Trichloroacetic acid and perchloric acid, with good protein aggregating ability, are desirably employed.

In the present invention, the term "transglutaminase formulation for binding application" means a mixed powder of transglutaminase-containing product and protein-containing product, or a set provided in the form of the two in separate packages. The mixed powder may be used as is, or water may be added to obtain an aqueous solution which is then either sprinkled or spread on the object being binded, or mixed with the object being binded for use. When provided as a set, the two powders may be mixed immediately prior to use and employed in the same manner as a mixed powder, or a transglutaminase-containing product and protein-containing material may be dissolved in water and the solution coated on or mixed with the objects being binded. To the extent that storage stability adequate for product handling and distribution is achieved, the form of the formulation is not limited to that of a powder and liquid formulations may be employed.

The protein-containing material blended into a formulation for binding application may be selected from among the above-described protein-containing materials. Milk protein comprised primarily of casein, highly water-soluble gelatins, and blood plasma protein comprised primarily of fibrin all make good additional components. Among gelatins, fish gelatin is particularly desirable. Transglutaminase formulation for binding application containing additional components in the form of gelatins afford extremely good binding strength. However, they tend to be relatively easily affected by protease. Thus, the application of the present invention affords a marked improvement in quality.

In the present invention, the term "transglutaminase formuration for Surimi product" refers to a formulation characterized by comprising a transglutaminase-containing product and at least one additional component selected from among the group consisting of protein-containing materials, calcium salts, alkali salts, and excipients.

The calcium salt may be any salt containing calcium, such as calcium lactate, calcium carbonate, hydrogen calcium phosphate, calcinated calcium, eggshell calcium, and seashell calcium. Any alkali salt that raises the pH of ground fish may be employed, readily employed examples of which are trisodium phosphate, sodium carbonate, hydrogen sodium carbonate, and calcified carbonate. Examples of protein-containing materials that are blended into transglutaminase formulations for Surimi product are sodium casein, potassium casein, soy protein, and wheat protein. Excipients in the form of sugars, starches, dextrin, sugar-alcohols, and the like may be employed. Dextrin, starches, lactose, and the like, which have little effect on flavor, are particularly desirable.

In the present invention, the conditions of the enzymatic reaction in the method for measuring protease activity, specifically, the reaction temperature and the ratio of transglutaminase activity to substrate, are desirably as close as possible to the conditions of the protein-containing material following addition of the transglutaminase formulation. The ratio of transglutaminase activity to dimethylcasein during the enzymatic reaction in the method of measuring protease activity for formulations for binding application and surimi products is less than or equal to 200 units (TG activity/g dimethylcasein) (preferably less than or equal to 100 units (TG activity/g dimethylcasein)). The temperature during the enzymatic reaction is desirably not less than 0° C. but not greater than 10° C. for formulations for binding application, with 5° C. or more but not more than 10° C. being preferred, and desirably 30° C. or more but not more than 50° C. for Surimi products.

In the transglutaminase formulation for binding application of the present invention, the ratio of protease activity to transglutaminase activity (units of protease activity/units of transglutaminase activity) is desirably less than or equal to 0.00024, preferably less than or equal to 0.00017.

In the transglutaminase formulation for Surimi products of the present invention, the ratio of protease activity to transglutaminase activity (units of protease activity/units of transglutaminase activity) is desirably less than or equal to 0.002.

In the present invention, the term "unit of protease activity" is defined as follows: one unit (1U) is the amount of enzyme required to impart an increase in the colored substance in a nonprotein Lowry test solution by an amount equivalent to 1 mg of bovine serum albumin (BSA) in one minute. Since protease activity varies with measurement conditions, only values measured under identical measurement conditions can be directly compared.

The activity unit of transglutaminase in the present invention is measured and defined as follows: TG is reacted in a reaction system with a substrate in the form of benzylcarbonyl-L-glutamylglycine and hydroxylamine in pH 6.0 tris buffer solution at 37° C.; the hydroxamic acid produced is used to form an iron complex in the presence of trichloroacetic acid; absorbance is measured at 525 nm; the quantity of hydroxamic acid is obtained from a calibration curve; and the quantity of enzyme required to generate 1 µmole of hydroxamic acid per minute is defined as one unit (1U) (see Japanese Patent Application Publication No. S64-27471).

The method for measuring transglutaminase activity will be described in detail.

(Preparation of Reagent)

Reagent A: 0.03 M benzyloxycarbonyl-L-glutaminylglycine, 0.1 M hydroxylammonium chloride, 0.01 M reductive glutathione, 0.2 M trishydroxyaminomethane, pH 6.0 (pH adjusted with hydrochloric acid)

Reagent B: 3 M hydrochloric acid, 12 percent trichloroacetic acid, and 5 percent $FeCl_3.6H_2O$ in 0.1 M HCl prepared as a 1:1:1 mixture by volume.

Enzyme solution: The equivalent of 100 units of transglutaminase-containing product were accurately weighed out (the quantity weighed out was recorded) and dissolved in 50 mL of 0.2 M trishydrochloric acid buffer at pH 6.0 to prepare the enzyme solution.

(Operation)

A 0.2 mL quantity of enzyme solution was weighed out and charged to a test tube, 2 mL of reagent A was added at a temperature of 37° C., the mixture was reacted for 10 minutes at 37° C., 2 mL of reagent B was added to stop the reaction, the mixture was centrifuged for 10 minutes at 3,000 rpm, and the absorbance of the supernatant was measured at 525 nm (enzyme reaction segment). As a control, the same operation was conducted up through stopping the reaction but without admixing enzyme solution. A 0.2 mL quantity of enzyme solution was added, the mixture was centrifuged for 10 minutes at 3,000 rpm, and the absorbance of the supernatant was measured at 525 nm. The difference in absorbance of the enzyme reaction segment and the control was calculated.

Separately, instead of enzyme solution, an aqueous solution of 1 to 4 mg/mL of L-glutamic acid γ-monohydroxamic acid was employed, the same operations were conducted, the absorbance was measured, and a calibration curve was prepared.

(Calculation of Transglutaminase Activity)

The quantity of hydroxamic acid produced by the enzymatic reaction was obtained from the calibration curve and the above-described difference in absorbance. An enzymatic activity purifying one μmole of hydroxamic acid per minute was adopted as one unit (1 U), and the transglutaminase activity per gram of transglutaminase-containing product was calculated.

EMBODIMENTS

The present invention is described in detail below through measurement examples, experimental examples, and embodiments. However, the present invention is not limited thereto.

Measurement Example 1

<Method of Testing Low-Temperature Protease Activity in Transglutaminase-Containing Product>

(Method of Preparing Sample Solution)

Sample transglutaminase-containing product (product name: Activa TG, made by Ajinomoto Corp., about 1,000 units/g, powder) was weighed out and charged to a beaker and the quantity employed was recorded. The quantity employed in each test segment was separately indicated. A 100 mL quantity of 2 percent KCl and 1 percent Triton X-100 50 mM phosphate buffer (pH 6.0) was added. The mixture was stirred for 60 minutes and centrifuged (3,000 rpm, 10 minutes, 20° C.). The supernatant was passed through a syringe filter with a pore diameter of 0.45 μm (prepared at time of use). (Method of preparing dimethylcasein solution: Sigma C9801, Casein, N,N-dimethylated from bovine milk).

Dimethylcasein was accurately weighed out (the quantity employed in each test segment was separately specified), 100 mL of 50 mM phosphate buffer (pH 6.0) was added, and the mixture was dissolved by stirring for 30 minutes or more at ordinary temperature (prepared at time of use).

<Method of Preparing Lowry Test Solution>

Alkali copper test solution: 2 Percent $Na_2CO_3$ in 0.1 M NaOH, 2 percent sodium tartrate solution, and 1 percent copper sulfate pentahydrate were admixed in a 50:1:1 ratio (prepared at time of use).

Two-fold diluted phenol test solution (phenol reagent made by Wako Junyaku) and distilled water were admixed in a 1:1 ratio by volume (prepared at time of use).

<Measurement Operation>

(Enzymatic Reaction)

Sample: A dimethylcasein solution was placed in a thermostatic vessel set to a prescribed temperature ±0.5° C. (the temperature was confirmed with a standard temperature gage). A 0.4 mL quantity of the test solution was weighed and charged to a test tube and placed for 10 minutes or more in a thermostatic vessel. A 2 mL quantity of dimethylcasein solution was added and the mixture was immediately mixed by shaking. The mixture was then left standing for precisely a prescribed period at a prescribed temperature ±0.5° C. to allow the enzymatic reaction to progress (the temperature and standing period of each test segment were separately specified). When the reaction had ended, 2 mL of 5 percent trichloroacetic acid was added and the mixture was immediately stirred. The mixture was restored to room temperature. The mixture was charged to a thermostatic vessel set to 37° C.±0.5° C., left standing for 30 to 45 minutes, centrifuged (3,000 rpm, 10 minutes, 20° C.), and passed through a 0.45 μm syringe filter. The filtrate was recovered.

Blank: A 2 mL quantity of dimethylcasein was added to a test tube and left standing for precisely a prescribed period at a prescribed temperature ±0.5° C. (the temperature and standing period of each test segment were separately specified). A 2 mL quantity of 5 percent trichloroacetic acid was added. The mixture was immediately stirred and then placed at room temperature. A 0.4 mL quantity of test solution was added and the mixture was immediately stirred. The mixture was placed in a thermostatic vessel set to 37° C.±0.5° C. and left standing for 30 to 40 minutes, centrifuged (3,000 rpm, 10 minutes, 20° C.), and passed through a syringe filter with a pore size of 0.45 μm. The filtrate was recovered.

(Coloration Reaction)

A 0.4 mL quantity of filtrate was weighed out and charged to a test tube and 2 mL of alkali copper test solution was added. The mixture was stirred with shaking and left standing for 10 minutes at room temperature. Next, 0.2 mL of phenol reagent (made by Wako Junyaku).that had been diluted two-fold with water was added and-the mixture was immediately stirred. Next, the mixture was placed in a thermostatic vessel set to 37° C.±0.5° C., left standing for 30 minutes, and cooled to room temperature. The absorbance (the absorbance of the sample was denoted as Al and that of the blank as A2) at a wavelength of 700 nm was measured for the sample and water as control.

<Preparation of a Calibration Curve>

Commercial standard purified bovine serum albumin (BSA) solution (Bio-Rad Protein Assay Standard II, known concentration) was repeatedly diluted two-fold (1->2) with distilled water to prepare two-fold, four-fold, and eight-fold diluted solutions (for example, when the concentration of the BSA solution was 1.2 mg/mL, the concentrations of the diluted solutions were 0.6, 0.3, 0.15 mg/mL). A 0.4 mL quantity of diluted BSA solution was weighed out and charged to a test tube, 2 mL of alkali copper test solution was added, the components were mixed by stirring, and the mixture was left standing for 10 minutes at room temperature. Next, 0.2 mL of phenol reagent diluted two-fold with water was added and the mixture was immediately stirred. The mixture was placed in a thermostatic vessel set to 37° C.±0.5° C., left standing for 30 minutes, and then cooled to room temperature. The absorbance (S1) of this solution was measured at a wavelength of 700 nm employing water as control. Separately, distilled water was employed instead of BSA solution, the same operations were conducted, and the absorbance (S0) was measured. Employing the concentrations of various standard protein solutions and absorbance differences obtained by subtracting S0 from S1, a scatter diagram was prepared with the Microsoft software application Excel, an approximation curve was prepared as a second degree polynomial approximation, and a mathematical equation was obtained. Values obtained by subtracting S0 from absorbances A1 and A2 were substituted into the equation to calculate the protein concentrations (PA1, PA2).

<Method of Calculating Activity>

The quantity of enzyme that imparted an increase in the colored substance in nonprotein Lowry test solution by an amount equivalent to 1 mg of bovine serum albumin in one minute was defined as one unit (1U) and calculated based on the following equation.

Equation: Protease activity $(U/g) = (PA1 - PA2) \times 4.4 \div 0.4 \div T \times V \div W$ The symbols in the equation denote the following:

| | |
|---|---|
| PA1 | Protein concentration of the enzyme reaction solution (mg BSA/mL) |
| PA2 | Protein concentration of blank (mg BSA/mL) |
| 4.4 ÷ 0.4 | Coefficient of conversion to total solution quantity at end of reaction |
| T | Reaction time (minutes) |
| V | Dissolved volume of powder sample (mL) |
| W | Quantity of powder sample employed (g) |

Embodiment 1

Twelve lots of transglutaminase-containing product cultured at different times were prepared and the transglutaminase activity thereof was measured. Dextrin was admixed to adjust the transglutaminase activity of each lot to 1,000 units/g. These samples were then employed as transglutaminase-containing products.

Next, a formulation for binding application was prepared by the method described further below and the binding strength thereof was measured. In accordance with the method indicated in Measurement Example 1, the quantity of sample transglutaminase-containing product to be employed, the quantity of dimethylcasein to be employed, and the reaction time and temperature during the enzymatic reaction were set in accordance with Table 1. The protease activity of the 12 lots of sample transglutaminase-containing product were then measured under multiple conditions. Finally, a correlation coefficient of protease activity to binding strength measured under various conditions was calculated using the Microsoft application Excel. The effect of protease activity measurement conditions was then compared based on the correlation between protease activity and binding strength.

<Method of Preparing Formulation for Binding Application>

Employing the sample transglutaminase-containing products of 12 lots, powder starting materials were mixed in the ratio indicated below.

| | |
|---|---|
| Sample transglutaminase-containing product (1,000 units/g): | 4.5 parts |
| Fish gelatin powder | 40 parts |
| Dextrin powder | 53.5 parts |
| Fine silicon dioxide powder | 2 parts |

(The transglutaminase activity/substrate ratio of this mixture was 112 units/g.)

<Method of Measuring Binding Strength>

(1) Pieces of beef round were shaped into 2×2 cm cubes.
(2) The formulation for binding application was sprinkled on one surface of each shaped beef cube. The surfaces of two cubes of beef on which the formulation had been sprinkled were binded and the cubes were packaged under vacuum, subjected to pressure, and left standing for 72 hours at 5° C.
(3) The binded beef cubes were subjected to breaking force with a texture analyzer, the peak breaking stress was measured, and the value obtained was adopted as the binding force.
(4) The binding force was divided by the adhesion surface area (four square centimeters) to obtain the binding strength. The binding strength was denoted in units of g/cm². The correlation between the common logarithm of the binding strength and the protease activity value was determined.

<The Correlation Between Binding Strength and Protease Activity>

(Denoted as the Concentration of the Solution Employed)

TABLE 1

Table 1) Correlation between measurement conditions and binding strength

| | | Quantity employed during solution preparation (per 100 mL of solution) | | Ratio of concentrations of various components during enzymatic reaction | | Ratio of transglutaminase activity/ casein | Reaction temperature and time | | Correlation coefficient |
|---|---|---|---|---|---|---|---|---|---|
| | | Qty of sample trans-glutaminase-containing product employed (g) | Quantity of dimethylcasein employed (g) | Transglutaminase activity concentration (units/100 mL) | Dimethylcasein concentration (g/100 mL) | during reaction (units/g) | Reaction temperature (° C.) | Reaction time (hours) | with binding strength |
| Emb. 1 | Invention | 0.10 | 0.50 | 16.7 | 0.417 | 40 | 55 | 1 | −0.883 |
| Emb. 2 | Comp. Ex. | 5.00 | 0.50 | 833.3 | 0.417 | 2000 | 55 | 1 | −0.656 |
| Emb. 3 | Invention | 0.10 | 0.50 | 16.7 | 0.417 | 40 | 37 | 1 | −0.867 |
| Emb. 4 | Comp. Ex. | 5.00 | 0.50 | 833.3 | 0.417 | 2000 | 37 | 1 | −0.677 |
| Emb. 5 | Invention | 0.10 | 0.50 | 16.7 | 0.417 | 40 | 5 | 24 | −0.919 |
| Emb. 6 | Invention | 0.50 | 0.50 | 83.3 | 0.417 | 200 | 5 | 24 | −0.928 |
| Emb. 7 | Invention | 0.50 | 2.50 | 83.3 | 2.083 | 40 | 5 | 24 | −0.953 |

TABLE 1-continued

Table 1) Correlation between measurement conditions and binding strength

| | | Quantity employed during solution preparation (per 100 mL of solution) | | Ratio of concentrations of various components during enzymatic reaction | | Ratio of transglutaminase activity/ casein | Reaction temperature and time | | Correlation coefficient |
|---|---|---|---|---|---|---|---|---|---|
| | | Qty of sample trans-glutaminase-containing product employed (g) | Quantity of dimethylcasein employed (g) | Transglutaminase activity concentration (units/100 mL) | Dimethylcasein concentration (g/100 mL) | during reaction (units/g) | Reaction temperature (° C.) | Reaction time (hours) | with binding strength |
| Emb. 8 | Comp. Ex. | 5.00 | 0.50 | 833.3 | 0.417 | 2000 | 5 | 24 | −0.742 |
| Emb. 9 | Invention | 0.50 | 5.00 | 83.3 | 4.167 | 20 | 5 | 24 | −0.951 |

*The transglutaminase activity of the original transglutaminase powder was rendered a uniform 1,000 units/g in advance.

Based on Table 1, it will be understood that the ratio of transglutaminase activity to substrate during the reaction and the temperature during the reaction affected the correlation.

In the comparative examples, the correlation between binding strength and protease activity indicated by the correlation coefficient (the correlation increasing with the distance from 0) was low, and it was difficult to estimate the quality (binding strength) of the formulation for binding application from the protease activity of the transglutaminase-containing product. However, for the invention, the correlation was quite high, making it possible to estimate with good precision the quality of the formulation for binding application.

Here, the term "correlation coefficient" refers to a coefficient denoting the strength of the relation between two variables (here, binding strength and protease activity). The coefficient ranges from −1 to 1. A scatter diagram of the two variables was drawn. A slope rising upward to the right indicates a positive correlation, and a slope falling to the right indicates a negative correlation. The closer the correlation coefficient approaches zero, the weaker the correlation between the two variables.

Table 2 gives the various protease activities for the multiple lots of transglutaminase-containing product measured under the conditions of a comparative example (Embodiment 4) and the present invention (Embodiment 7), and the binding strengths of the formulations for binding application prepared using the transglutaminase-containing compounds of these lots. FIG. 1 shows a scatter diagram of particular protease activity plotted against the common logarithm of binding strength, and a linear approximation for the scattered values of the present invention (Embodiment 7).

TABLE 2

Table 2) Examples of measurement values of a comparative example (Embodiment 4) and the present invention (Embodiment 7)

| Lot | Comp. Ex. (Emb. 4) | Present Invention (Emb. 7) | Binding strength | Log10 (binding strength) |
|---|---|---|---|---|
| A | 0.933 | 0.391 | 9 | 0.96 |
| B | 0.828 | 0.262 | 56 | 1.75 |
| C | 0.800 | 0.117 | 132 | 2.12 |
| D | 0.992 | 0.156 | 156 | 2.19 |
| E | 0.609 | 0.085 | 157 | 2.20 |
| F | 0.408 | 0.098 | 185 | 2.27 |
| G | 0.396 | 0.090 | 283 | 2.45 |
| H | 0.320 | 0.051 | 293 | 2.47 |
| I | 0.460 | 0.093 | 278 | 2.44 |
| J | 0.204 | 0.057 | 291 | 2.46 |
| K | 0.244 | 0.033 | 299 | 2.48 |
| L | 0.220 | 0.060 | 151 | 2.18 |
| Correlation | −0.677 | −0.953 | | |

The linear approximation expression for scattering of the present invention (Embodiment 7) is as follows: Log 10(binding strength(g/cm$^2$))=−4.011×protease activity (units/g transglutaminase-containing product)+2.6626

The practical minimum binding strength is considered based on experience to be 50 g/cm$^2$, preferably 100 g/cm$^2$. Calculation of the protease activity for the common logarithm 1.70 for a binding strength of 50 g/cm$^2$ and for the common logarithm 2.00 for 100 g using the linear approximation curve of the present invention (Embodiment 7) of FIG. 1 yields values of 0.24 unit/g and 0.17 unit/g, respectively. Accordingly, imparting a practical binding strength to a formulation for binding application requires a protease activity in the transglutaminase-containing product of 0.24 unit or less per gram of transglutaminase-containing product (containing 1,000 units of transglutaminase activity per gram), preferably 0.17 unit or less, that is, 0.00024 (unit of protease activity/unit of transglutaminase activity) or less, preferably 0.0017 (unit of protease activity/unit of transglutaminase activity) or less based on the measurement method of the present invention (Embodiment 7).

Embodiment 2

Sixteen lots of transglutaminase-containing product cultured at different times were prepared and the transglutaminase activity thereof was measured. Dextrin was admixed to adjust the transglutaminase activity of each lot to 1,000 units/g. These samples were then employed as transglutaminase-containing products.

Next, a formulation for Surimi products was prepared by a method described further below, that formulation was employed to prepare boiled fish paste (a Surimi product) by a method described further below, and the physical properties of the boiled fish paste were measured. In accordance with the method indicated in Measurement Example 1, the quantity of sample transglutaminase-containing product to be employed, the quantity of dimethylcasein to be employed, and the reaction time and temperature during the enzymatic reaction were set in accordance with Table 3. The protease activity of the 16 lots of sample transglutaminase-containing product were then measured under multiple conditions. Finally, a correlation coefficient of the protease activity and physical properties (breaking stress) of the boiled fish paste that were measured under the various conditions was calculated using the Microsoft application Excel. The effect of protease activity measurement conditions was then compared based on the correlation between protease activity and the physical properties of the boiled fish paste.

<Method of Preparing a Formulation for Surimi Products>

Employing the sample transglutaminase-containing products of 16 lots, powder starting materials were mixed in the ratio indicated below.

| Sample transglutaminase-containing product | 10 parts |
|---|---|
| Calcium lactate | 75 parts |
| Dextrin | 15 parts |

<Method of Preparing Boiled Fish Paste>

A 1,000 g quantity of flaked frozen ground fish (Alaska pollack, FA grade) was cut until the temperature reached −2 to 0° C. with a Stephan cutter. A 30 g quantity of table salt was added, 350 g of ice water was added, and cutting was conducted until the temperature reached 7 to 8° C. with the Stephan cutter. To this were added 20 g of granulated sugar, 40 g of potato starch, 350 g of ice water, and 2 g of Surimi product formulation. Cutting was conducted until the temperature reached 7 to 8° C. The material thus obtained was stuffed into a cylindrical vinylidene chloride casing 30 mm in diameter, heated for 30 minutes in 40° C. steam and then for 20 minutes in 85° C. steam, and cooled by immersion in ice water.

<Method of Measuring the Physical Properties of Boiled Fish Paste>

A breaking test was conducted with a texture analyzer. Cylindrical pieces of boiled fish paste were cut to heights of 30 mm, a spherical plunger 5 mm in diameter was pushed at a rate of 1 mm/s into the center of the cross-section of the boiled fish paste, and the stress at the moment of breaking (breaking stress) was measured. Correlation coefficients for the boiled fish paste breaking stress and the protease activity under various conditions of the sample transglutaminase-containing product were obtained using the Microsoft application Excel.

<Correlation of the Physical Properties of Boiled Fish Paste and Protease Activity>

(Recording of the Concentration of the Solution Employed)

TABLE 3

Table 3) Correlation between measurement conditions and physical properties of boiled fish paste

| | | Quantity employed during solution preparation (per 100 mL of solution) | | Ratio of concentrations of various components during enzymatic reaction | | | Reaction temperature and time | | Correlation coefficient |
|---|---|---|---|---|---|---|---|---|---|
| | | Qty of sample transglutaminase-containing product employed (g) | Quantity of dimethylcasein employed (g) | Transglutaminase activity concentration (units/100 mL) | Dimethylcasein concentration (g/100 mL) | Ratio of transglutaminase activity/casein during reaction (units/g) | Reaction temperature (° C.) | Reaction time (hours) | with binding strength |
| Emb. 10 | Comp. Ex. | 5.00 | 0.50 | 833.3 | 0.417 | 2000 | 40 | 1 | −0.480 |
| Emb. 11 | Invention | 0.50 | 2.50 | 83.3 | 2.083 | 40 | 5 | 24 | −0.488 |
| Emb. 12 | Invention | 0.50 | 2.50 | 83.3 | 2.083 | 40 | 40 | 1 | −0.552 |

*The transglutaminase activity of the original transglutaminase powder was rendered a uniform 1,000 units/g in advance.

Based on Table 3, the correlation of the method of the present invention was greater than that of the comparative example, permitting the estimation with good precision of the effect on Surimi products.

A linear approximation expression prepared for the scatter diagram of the protease activity and breaking strength of the present invention (Embodiment 12), and the average breaking strength, are given below.

Breaking strength (g)=−22.44×protease activity (unit/g transglutaminase-containing material)+ 460.8

Average breaking strength: 436 g

Based on experience, no functional difference in taste is experienced and the quality of a Surimi product formulation is determined as falling within the permissible range when the breaking strength of boiled fish paste is greater than or equal to 95 percent of the standard. Employing the average value as the standard, when the protease activity corresponding to the average breaking strength×95 percent=436×95 percent=415 g was obtained from the above linear approximation expression, a value of 2.06 units/g was obtained. Accordingly, to ensure practical quality as a Surimi product formulation, the protease activity of the transglutaminase-containing product when employing the measurement method of the present invention (Embodiment 12) was thought to require two units or less per gram of transglutaminase-containing product (containing 1,000 units of transglutaminase activity per gram), or less than or equal to 0.02 (units of protease activity/ units of transglutaminase activity).

INDUSTRIAL APPLICABILITY

Based on the method for measuring protease activity of the present invention, the effect of a formulation when a transglutaminase formulation is employed in a protein-containing material can be readily determined from the protease activity of the transglutaminase-containing material.

Further, application of the above-described measurement method permits the ready selection of a transglutaminase-containing product that can be used to constitute a transglutaminase formulation exhibiting desired effects from various available transglutaminase-containing products.

Further, application of the above-described measurement method permits the ready selection of a transglutaminase-containing product that can be used to constitute a transglutaminase formulation exhibiting desired binding effects from various available transglutaminase-containing products.

Further, application of the above-described measurement method permits the ready selection of a transglutaminase-containing product that can be used to constitute a transglutaminase formulation exhibiting desired effects on Surimi products from various available transglutaminase-containing products.

The invention claimed is:

1. A method for selecting a microbial transglutaminase formulation for binding application comprising:
   (a) measuring a protease activity of a plurality of microbial transglutaminase-containing products by a measurement method; and
   (b) selecting a microbial transglutaminase-containing product with a ratio of protease activity to transglutaminase activity (units of protease activity/units of transglutaminase activity) no more than 0.00024, wherein said measurement method comprises:
   (i) preparing an aqueous solution of a microbial transglutaminase-containing product and an aqueous solution of a protease substrate in the form of dimethylcasein so that the ratio of transglutaminase activity to the quantity of dimethylcasein is 200 units/g or less;
   (ii) conducting an enzymatic reaction based on protease;
   (iii) adding an acid and filtering; and
   (iv) measuring the concentration of said protease substrate in the filtrate.

2. The method of claim 1, wherein said enzymatic reaction based on protease is conducted at a temperature of not less than 0° C. and not greater than 10° C.

3. The method of claim 2, wherein said ratio of protease activity to transglutaminase activity is no more than 0.00017.

4. The method of claim 1, wherein measurement of the protease activity in the microbial transglutaminase-containing product is conducted under the following conditions:
   (I-a) preparing a solution of sample microbial transglutaminase-containing product and a solution of protease substrate in the form of dimethylcasein in a such a manner as to yield 2.4 parts of a pH 6 aqueous solution with a transglutaminase activity of 83.3 units/100 mL and a dimethylcasein content of 2.083 g/100 mL;
   (I-b) conducting an enzymatic reaction based on the protease by mixing the solution of microbial transglutaminase-containing product and aqueous solution of dimethylcasein and allowing the mixture to stand for 24 hours at 5° C.;
   (I-c) obtaining a sample filtrate by adding two parts of 12 percent trichioroacetic acid, centrifuging the mixture, and filtering the supernatant;
   (II-a) preparing two parts of a pH 6 aqueous solution comprising 2.5 g/100 mL of dimethylcasein solution;
   (II-b) allowing the dimethylcasein aqueous solution to stand for 24 hours at 5° C.;
   (II-c) adding two parts of 12 percent trichioroacetic acid, adding 0.4 part of a solution of 500 units/100 mL of sample transglutaminase-containing product, mixing, centrifuging the mixture, and filtering the supernatant to obtain a blank filtrate;
   (d) causing a coloration reaction by the Lowry method in the sample solution and blank filtrate, measuring the absorbance of each solution at a wavelength of from 500 to 700 nm employing distilled water as control, denoting the absorbance of the sample filtrate as A1 and the absorbance of the blank filtrate as A2, separately causing a coloration reaction by the Lowry method in standard purified bovine serum albumin solution of known concentration, measuring the absorbance at a wavelength of from 500 to 700 nm employing distilled water as control, creating a calibration curve from the absorbance of the standard purified bovine serum albumin solution and the absorbance of the distilled water, calculating the protein concentration of the sample filtrate and blank (PA1, PA2) from absorbance values A1 and A2, and obtaining the protease activity from the following equation:

protease activity (units/g)=($PA1-PA2$)× 4.4÷0.4÷1440×$V$÷$W$ wherein:

PA1 denotes the protein concentration of the sample filtrate (mg BSA/mL);

-continued

| | |
|---|---|
| PA2 | denotes the protein concentration of the blank (mg BSA/mL); |
| 4.4 ÷ 0.4 | denotes the coefficient of conversion to the total quantity of the solution at the end of the reaction; |
| 1440 | denotes the number of minutes in a reaction time of 24 hours; |
| V | denotes the dissolved volume of sample microbial transglutaminase-containing product (mL); and |
| W | denotes the quantity of sample microbial transglutaminase-containing product employed (g). |

5. The method of claim 4, wherein said ratio of protease activity to transglutaminase activity is no more than 0.00017.

6. The method of claim 1, wherein said ratio of protease activity to transglutaminase activity is no more than 0.00017.

7. A method for selecting a microbial transglutaminase formulation for binding application comprising:
   (a) measuring the protease activity of a microbial transglutaminase-containing product; and
   (b) selecting a protein-containing material and a microbial transglutaminase-containing product with a ratio of protease activity to transglutaminase activity (units of protease activity/units of transglutaminase activity) no more than 0.00024 for use,
   wherein said measuring the protease activity of a microbial transglutaminase-containing product comprises:
   (i) preparing an aqueous solution of a microbial transglutaminase-containing product and an aqueous solution of a protease substrate in the form of dimethylcasein so that the ratio of transglutaminase activity to the quantity of dimethylcasein is 200 units/g or less;
   (ii) conducting an enzymatic reaction based on protease;
   (iii) adding an acid and filtering; and
   (iv) measuring the concentration of said protease substrate in the filtrate.

8. The method according to claim 7, wherein said protein-containing material is gelatin.

9. The method of claim 7, wherein said enzymatic reaction based on protease is conducted at a temperature of not less than 0° C. and not greater than 10° C.

10. The method of claim 9, wherein said ratio of protease activity to transglutaminase activity is no more than 0.00017.

11. The method of claim 7, wherein measurement of the protease activity in the microbial transglutaminase-containing product is conducted under the following conditions:
   (I-a) preparing a solution of sample microbial transglutaminase-containing product and a solution of protease substrate in the form of dimethylcasein in a such a manner as to yield 2.4 parts of a pH 6 aqueous solution with a transglutaminase activity of 83.3 units/100 mL and a dimethylcasein content of 2.083 g/100 mL;
   (I-b) conducting an enzymatic reaction based on the protease by mixing the solution of microbial transglutaminase-containing product and aqueous solution of dimethylcasein and allowing the mixture to stand for 24 hours at 5° C.;
   (I-c) obtaining a sample filtrate by adding two parts of 12 percent trichloroacetic acid, centrifuging the mixture, and filtering the supernatant;
   (II-a) preparing two parts of a pH 6 aqueous solution comprising 2.5 g/100 mL of dimethylcasein solution;
   (II-b) allowing the dimethylcasein aqueous solution to stand for 24 hours at 5° C.;
   (II-c) adding two parts of 12 percent trichloroacetic acid, adding 0.4 part of a solution of 500 units/100 mL of sample transglutaminase-containing product, mixing, centrifuging the mixture, and filtering the supernatant to obtain a blank filtrate;
   (d) causing a coloration reaction by the Lowry method in the sample solution and blank filtrate, measuring the absorbance of each solution at a wavelength of from 500 to 700 nm employing distilled water as control, denoting the absorbance of the sample filtrate as A1 and the absorbance of the blank filtrate as A2, separately causing a coloration reaction by the Lowry method in standard purified bovine serum albumin solution of known concentration, measuring the absorbance at a wavelength of from 500 to 700 nm employing distilled water as control, creating a calibration curve from the absorbance of the standard purified bovine serum albumin solution and the absorbance of the distilled water, calculating the protein concentration of the sample filtrate and blank (PA1, PA2) from absorbance values A1 and A2, and obtaining the protease activity from the following equation:

protease activity (units/g)=(PA1−PA2)× 4.4÷0.4÷1440×V÷W wherein:

| | |
|---|---|
| PA1 | denotes the protein concentration of the sample filtrate (mg BSA/mL); |
| PA2 | denotes the protein concentration of the blank (mg BSA/mL); |
| 4.4 ÷ 0.4 | denotes the coefficient of conversion to the total quantity of the solution at the end of the reaction; |
| 1440 | denotes the number of minutes in a reaction time of 24 hours; |
| V | denotes the dissolved volume of sample microbial transglutaminase-containing product (mL); and |
| W | denotes the quantity of sample microbial transglutaminase-containing product employed (g). |

12. The method of claim 7, wherein said ratio of protease activity to transglutaminase activity is no more than 0.00017.

13. A method for selecting a microbial transglutaminase formulation for Surimi product, comprising:
   (a) measuring the protease activity of a plurality of microbial transglutaminase-containing products by a measurement method; and
   (b) selecting a microbial transglutaminase-containing product with a ratio of protease activity to transglutaminase activity (units of protease activity/units of transglutaminase activity) no more than 0.002,
   wherein said measurement method comprises:
   (i) preparing an aqueous solution of a microbial transglutaminase-containing product and an aqueous solution of a protease substrate in the form of dimethylcasein so that the ratio of transglutaminase activity to the quantity of dimethylcasein is 200 units/g or less;
   (ii) conducting an enzymatic reaction based on protease;
   (iii) adding an acid and filtering; and
   (iv) measuring the concentration of said protease substrate in the filtrate.

14. The method of claim 13, comprising conducting an enzymatic reaction based on said protease at a temperature of not less than 30° C. but not greater than 50° C.

15. The method of claim 13, wherein said measurement of the protease activity in the microbial transglutaminase-containing product is conducted under the following conditions:
   (I-a) preparing a solution of sample microbial transglutaminase-containing product and a solution of protease substrate in the form of dimethylcasein in a such a manner as to yield 2.4 parts of a pH 6 aqueous solution with a transglutaminase activity of 83.3 units/100 mL and a dimethylcasein content of 2.083 g/100 mL;

(I-b) conducting an enzymatic reaction based on the protease by mixing the solution of microbial transglutaminase-containing product and aqueous solution of dimethylcasein and allowing the mixture to stand for 1 hour at 40° C.;

(I-c) obtaining a sample filtrate by adding two parts of 12 percent trichioroacetic acid, centrifuging the mixture, and filtering the supernatant;

(II-a) preparing two parts of a pH 6 aqueous solution comprising 2.5 g/100 mL of dimethylcasein solution;

(II-b) allowing the dimethylcasein aqueous solution to stand for 1 hour at 40° C.;

(II-c) adding two parts of 12 percent trichloroacetic acid, adding 0.4 part of a solution of 500 units/IGO mL of sample transglutaminase-containing product, mixing, centrifuging the mixture, and filtering the supernatant to obtain a blank filtrate;

(d) causing a coloration reaction by the Lowry method in the sample solution and blank filtrate, measuring the absorbance of each solution at a wavelength of from 500 to 700 nm employing distilled water as control, denoting the absorbance of the sample filtrate as A1 and the absorbance of the blank filtrate as A2, separately causing a coloration reaction by the Lowry method in standard purified bovine serum albumin solution of known concentration, measuring the absorbance at a wavelength of from 500 to 700 nm employing distilled water as control, creating a calibration curve from the absorbance of the standard purified bovine serum albumin solution and the absorbance of the distilled water, calculating the protein concentration of the sample filtrate and blank (PA1, PA2) from absorbance values A1 and A2, and obtaining the protease activity from the following equation:

$$\text{protease activity (units/g)} = (PA1-PA2) \times 4.4 \div 0.4 \div 60 \times V \div W$$

wherein:

| | |
|---|---|
| PA1 | denotes the protein concentration of the sample filtrate (mg BSA/mL); |
| PA2 | denotes the protein concentration of the blank (mg BSA/mL); |
| 4.4 ÷ 0.4 | denotes the coefficient of conversion to the total quantity of the solution at the end of the reaction; |
| 60 | denotes the number of minutes in a reaction time of 1 hour; |
| V | denotes the dissolved volume of sample microbial transglutaminase-containing product (mL); and |
| W | denotes the quantity of sample microbial transglutaminase-containing product employed (g). |

16. A method for selecting a microbial transglutaminase formulation for Surimi product, comprising:

(a) measuring the protease activity of a microbial transglutaminase-containing product; and (b) selecting a microbial transglutaminase-containing product with a ratio of protease activity to transglutaminase activity (units of protease activity/units of transglutaminase activity) no more than 0.002, and at least one additional component selected from the group consisting of calcium salts, alkali salts, and protein-containing materials, wherein said measuring the protease activity of a microbial transglutaminase-containing product comprises:

(i) preparing an aqueous solution of a microbial transglutaminase-containing product and an aqueous solution of a protease substrate in the form of dimethylcasein so that the ratio of transglutaminase activity to the quantity of dimethylcasein is 200 units/g or less;

(ii) conducting an enzymatic reaction based on protease;

(iii) adding an acid and filtering; and (iv) measuring the concentration of the said protease substrate in the filtrate.

17. The method of claim 16, comprising conducting an enzymatic reaction based on said protease at a temperature of not less than 30° C. but not greater than 50° C.

18. The method of claim 16, wherein said measurement of the protease activity in the microbial transglutaminase-containing product is conducted under the following conditions:

(I-a) preparing a solution of sample microbial transglutaminase-containing product and a solution of protease substrate in the form of dimethylcasein in a such a manner as to yield 2.4 parts of a pH 6 aqueous solution with a transglutaminase activity of 83.3 units/100 mL and a dimethylcasein content of 2.083 g/100 mL;

(I-b) conducting an enzymatic reaction based on the protease by mixing the solution of microbial transglutaminase-containing product and aqueous solution of dimethylcasein and allowing the mixture to stand for 1 hour at 40° C.;

(I-c) obtaining a sample filtrate by adding two parts of 12 percent trichloroacetic acid, centrifuging the mixture, and filtering the supernatant;

(II-a) preparing two parts of a pH 6 aqueous solution comprising 2.5 g/100 mL of dimethylcasein solution;

(II-b) allowing the dimethylcasein aqueous solution to stand for 1 hour at 40° C.;

(II-c) adding two parts of 12 percent trichloroacetic acid, adding 0.4 part of a solution of 500 units/100 mL of sample transglutaminase-containing product, mixing, centrifuging the mixture, and filtering the supernatant to obtain a blank filtrate;

(d) causing a coloration reaction by the Lowry method in the sample solution and blank filtrate, measuring the absorbance of each solution at a wavelength of from 500 to 700 nm employing distilled water as control, denoting the absorbance of the sample filtrate as A1 and the absorbance of the blank filtrate as A2, separately causing a coloration reaction by the Lowry method in standard purified bovine serum albumin solution of known concentration, measuring the absorbance at a wavelength of from 500 to 700 nm employing distilled water as control, creating a calibration curve from the absorbance of the standard purified bovine serum albumin solution and the absorbance of the distilled water, calculating the protein concentration of the sample filtrate and blank (PA1, PA2) from absorbance values A1 and A2, and obtaining the protease activity from the following equation:

$$\text{protease activity (units/g)} = (PA1-PA2) \times 4.4 \div 0.4 \div 60 \times V \div W$$

wherein:

| | |
|---|---|
| PA1 | denotes the protein concentration of the sample filtrate (mg BSA/mL); |
| PA2 | denotes the protein concentration of the blank (mg BSA/mL); |
| 4.4 ÷ 0.4 | denotes the coefficient of conversion to the total quantity of the solution at the end of the reaction; |
| 60 | denotes the number of minutes in a reaction time of 1 hour; |
| V | denotes the dissolved volume of sample microbial transglutaminase-containing product (mL); and |
| W | denotes the quantity of sample microbial transglutaminase-containing product employed (g). |

19. The method of claim 16, wherein said ratio of protease activity to transglutaminase activity is no more than 0.00017.

* * * * *